United States Patent
Allemeier et al.

(10) Patent No.: US 6,613,768 B1
(45) Date of Patent: Sep. 2, 2003

(54) TREATMENT OF FEMALE AROUSAL DISORDER

(75) Inventors: Lora L. Allemeier, Brookline, NH (US); Diane L. Brashear, Indianapolis, IN (US); Kenneth M. Ferguson, Seattle, WA (US); William E. Pullman, Far Hills, NJ (US)

(73) Assignee: Lilly ICOS LLC, Wilmington, DE (US)

( * ) Notice: Subject to any disclaimer, the term of this patent is extended or adjusted under 35 U.S.C. 154(b) by 0 days.

(21) Appl. No.: 10/031,321

(22) PCT Filed: Apr. 26, 2000

(86) PCT No.: PCT/US00/11128

§ 371 (c)(1),
(2), (4) Date: Oct. 19, 2001

(87) PCT Pub. No.: WO00/66114

PCT Pub. Date: Nov. 9, 2000

Related U.S. Application Data

(60) Provisional application No. 60/132,129, filed on Apr. 30, 1999.

(51) Int. Cl.[7] .............................................. A61K 31/495
(52) U.S. Cl. ....................................................... 514/250
(58) Field of Search ......................................... 514/250

(56) References Cited

U.S. PATENT DOCUMENTS

| | | |
|---|---|---|
| 4,507,323 A | 3/1985 | Stern |
| 4,521,421 A | 6/1985 | Foreman |
| 5,190,967 A | 3/1993 | Riley |
| 5,576,290 A | 11/1996 | Hadley |
| 5,703,112 A | 12/1997 | Foreman et al. |
| 5,731,339 A | 3/1998 | Lowrey |
| 5,773,457 A | 6/1998 | Nahoum |
| 5,877,216 A | 3/1999 | Place et al. |
| 5,886,039 A | 3/1999 | Kock et al. |
| 5,981,527 A | 11/1999 | Daugan et al. |
| 6,007,824 A | 12/1999 | Duckett et al. |
| 6,316,438 B1 * | 11/2001 | Yu et al. ................. 514/212.08 |

FOREIGN PATENT DOCUMENTS

| | | |
|---|---|---|
| EP | 0 951 908 | 10/1999 |
| WO | 99/21562 | 5/1999 |

OTHER PUBLICATIONS

Park et al., *Biochemical and Biophysical Research Communications, 249*, 612–617 (1998).
Nurnberg et al., *J. Clin. Psychiatry, 60*:1, 33–35 (1999).
Montejo–Gonzalez et al.,*Journal of Sex & Marital Therapy*, vol. 24, No. 3, pp. 176–194 (1997).
Halvorsen et al., *JABFP*, vol. 5, No. 2, pp. 177–192 (1992).
Leibulm, *International Journal of Impotence Research, 10, Supp. 2*, S104–S106 (1998).
Kaplan et al., *Urology 53*(3), pp. 481–486 (1999).
Fava et al., *Psychother Psychosom, 67*:328–331 (1998).
Berman et al., *Urology, 54*:385–391 (1999).
Berman et al., *International Journal of Impotence Research, 11, Suppl. 1*, S31–S38 (1999).
Tarcan et al., *The Journal of Urology*, vol. 161, pp. 940–944 (1999).
Azadzoi et al., *The Journal of Urology*, vol. 157, pp. 1011–1017 (1997).
Boston University School of Medicine, "New Perspectives in the Management of Female Sexual Dsyfunction," Abstracts, Oct. 22–24, 1999, Boston, MA.
Abstracts, *The Journal of Urology*, vol. 161, No. 4, pp. 178 and 210 (1999).
Butcher, *BMJ*, vol. 318, pp. 41–43 (1999).
Vroege et al., *Comprehensive Psychiatry*, vol. 39, No. 6, pp. 333–337 (1998).

* cited by examiner

*Primary Examiner*—Rebecca Cook
(74) *Attorney, Agent, or Firm*—Marshall, Gerstein & Borun

(57) ABSTRACT

A method of treating female arousal disorder (FAD) in a female patient is disclosed. The method includes orally administering an agent that inhibits cyclic guanosine 3'5'-monophosphate specific phosphodiesterase type 5 to the female patient.

4 Claims, No Drawings

TREATMENT OF FEMALE AROUSAL DISORDER

CROSS-REFERENCE TO RELATED APPLICATIONS

This is the U.S. national phase application of International Application No. PCT/US00/11128, filed on Apr. 26, 2000, which claims the benefit of provisional patent application Serial No. 60/132,129, filed Apr. 30, 1999.

FIELD OF THE INVENTION

The present invention relates to highly selective phosphodiesterase (PDE) enzyme inhibitors and to their use to treat female arousal disorder (FAD), also known as female sexual arousal disorder (FSAD). In particular, the present invention relates to potent inhibitors of cyclic guanosine 3',5'-monophosphate specific phosphodiesterase type 5 (PDE5) that, when administered as a pharmaceutical product, are useful for the treatment of FAD.

BACKGROUND OF THE INVENTION

Female sexual dysfunction (FSD) is a highly prevalent condition (R. T. Micheal et al., *Sex in America*, Little Brown, Boston, Mass. (1994)). However, in contrast to the overwhelming interest in treatment of male erectile dysfunction (MED) (Feldman et al. 1994, NIH Consensus Development Panel on Impotence 1993, Rosen et al. 1997, Sildenafil Study Group 1998), relatively little attention has been paid to sexual problems in women. There are few studies of the physiological process of the female sexual response, and there are few effective treatments available to women for sexual problems. Furthermore, a barrier to research and development in this area has been the lack of established diagnostic classifications, or of established endpoints, for testing new drugs in clinical trials for the treatment of FSD.

FSD has been used as a "catchall" phrase to include a variety of sexual disorders in woman including sexual desire disorders, sexual arousal disorders, orgasmic disorders, sexual pain disorders, vaginismus, dyspareunia, trauma from sexual contact, sexual inhibition, sexual panic disorders, childhood sexual abuse, and sexual addiction or compulsive behavior. From the multitude of disorders, The American Psychiatric Association, *Diagnostic and Statistical Manual, Mental Disorders, Ed.* 3, Washington, D.C., APA (1980) and the International Classification of Diseases (World Health Organization) have identified four major categories of female sexual dysfunction: (1) sexual desire disorders, (2) sexual arousal disorders, (3) orgasmic disorders, and (4) sexual pain disorders. Each of these categories can be further sub-typed as follows: lifelong versus acquired type; generalized versus situational type; etiologic classification (e.g., organic, psychogenic, mixed, unknown).

Sexual desire disorders are defined by the following two diagnoses. Hypoactive Sexual Desire Disorder (HSDD) is the persistent or recurrent deficiency (or absence) of sexual fantasies/thoughts and/or desire for, or receptivity to, sexual activity, which causes personal distress. Sexual Aversion Disorder is the persistent or recurrent phobic aversion to, and avoidance of, sexual contact with a sexual partner, which causes personal distress.

Sexual arousal disorders are defined as a recurrent inability to attain, or maintain until completion of sexual activity, an adequate lubrication/swelling response of sexual excitement. The arousal response consists of vasocongestion in the pelvis, vaginal lubrication, and expansion and swelling of external genitalia. The disturbance must cause marked distress or interpersonal difficulty.

Orgasmic disorders are defined as the persistent or recurrent difficulty, delay in, or absence of, attaining orgasm following sufficient sexual stimulation and arousal, which causes personal distress.

Sexual pain disorders are defined by the following three diagnoses. Dyspareunia is a recurrent or persistent genital pain associated with sexual intercourse. Vaginismus is a recurrent or persistent involuntary spasm of the musculature of the outer third of the vagina that interferes with vaginal penetration, which causes personal distress. Noncoital Sexual Pain Disorder is a recurrent or persistent genital pain induced by noncoital sexual stimulation.

Unfortunately, use of the term "female sexual dysfunction" as a catchall phrase to broadly encompass all disorders fails to distinguish the significant clinical and physiological differences between these disorders, and offers little guidance to the attending physician with respect to how to properly diagnose and prescribe pharmacological treatment. Because pharmacological treatment is not uniformly effective against all varieties of female sexual dysfunction, there remains a need in the art to identify which pharmacological therapy is useful to treat which sexual disorder.

Place et al. U.S. Pat. No. 5,877,216 discloses a method of treating sexual dysfunction in a female individual by administering a pharmaceutical formulation containing a selected vasodilating agent to the vagina and/or vulvar area of the individual undergoing treatment. The application is directed to prostaglandins, but additional vasodilation agents that are useful in conjunction with the invention are disclosed and include, inter alia, phosphodiesterase inhibitors. Phosphodiesterase inhibitors are not further defined. Neither PDE5 inhibitors or their use to treat female arousal disorder are disclosed.

EP 0 702 555 describes the method of treating male erectile dysfunction with a PDE inhibitor and particularly a PDE5 inhibitor. The patent application further suggests that a PDE inhibitor may be used for female sexual dysfunction, particularly orgasmic dysfunction related to clitoral disturbances. Neither PDE inhibitor, PDE5 inhibitor, nor female sexual dysfunction are defined further except by reference to compounds specifically disclosed and referenced to orgasmic dysfunction.

Sildenafil citrate (sildenafil, sold under the trademark VIAGRA®), is a known PDE5 inhibitor, and has been shown to facilitate erectile function in men suffering from MED. In particular, sildenafil amplifies the effect of central and peripheral physiologic signals resulting in cyclic guanosine monophosphate (cGMP) mediation of corpus cavernosum smooth muscle relaxation, leading in turn to vasodilation and blood pooling which produces an erection. While there are obvious external anatomical differences between male and female external genitalia, there also is a recognized tissue homology. In addition, there is accumulating evidence of analogous physiological responses (for example, relaxation of clitoral corpus cavernosum and genital vasodilation, K. Park et al., *Biochem. Biophys. Res. Commun.*, 249(3): 612–617 (1998)), in female sexual tissue. However, the clinical significance of a response in female sexual tissue, and what, if any, disorder this response correlates to has not been disclosed.

While sildenafil is approved for use in males, several publications have referenced clinical studies in women. M. Fava et al., in *Psychother. Psychosom.*, 67(6): 328–31 (1998), studied the effects of sildenafil on antidepressant-induced sexual dysfunction in 14 depressed patients (9 men and 5 women). Antidepressant-induced sexual dysfunction is generally characterized by a lack of desire (sexual desire disorder) and delayed orgasm and anorgasmia (orgasmic disorder), but also may include arousal difficulties, H. G. Nurnberg et al., *J. Clin. Psychiatry,* 60(1), 33–35 (1999). The study reports a statistically significant improvement in all domains of sexual functioning with a 69% rate of patients reporting improvement. However, the study fails to indicate the response by gender-(9 out of 14 patients were men). In addition, the study was not placebo controlled, and fails to correct the data for a placebo effect. The authors could not "rule out the possibility that clinical improvements in sexual functioning in our patients may be the result of nonspecific placebo-like effects." These shortcomings in the study leave a person skilled in the art unable to draw conclusions with respect to the efficacy of using sildenafil in treating sexual desire disorder and anorgasmia, and the study offers no motivation to study its usefulness to treat female arousal disorder.

Kaplan et al., in *Urology* 53(3):481–6 (1999), studied the safety and efficacy of sildenafil in postmenopausal woman with self-described sexual dysfunction. The form of sexual dysfunction being treated was not further defined or characterized. Sildenafil was studied in thirty-three postmenopausal women with sexual dysfunction. The study used the Female Sexual Function Index, which contains one question on vaginal dryness, with other questions focused on sexual desire, pain, satisfaction, and clitoral sensation. The study was not directed to arousal disorder. Six patients reported significant improvement in therapeutic response. Improvement in lubrication and clitoral sensation improved by 0.54 (23.2%) and 0.67 (31.3%), respectively. Clitoral discomfort and "hypersensitivity" occurred in 7 woman (3 of whom withdrew from the study). While the authors concluded that sildenafil is well tolerated in postmenopausal women, they also concluded that sildenafil did-not significantly improve overall sexual function.

Finally, sildenafil was studied for the treatment of iatrogenic serotonergic antidepressant medication-induced sexual dysfunction in four patients (two men, two woman) by H. G. Nurnberg et al. in *J. Clin. Psychiatry,* 60(1):33–5 (1999). The antidepressant medication-induced dysfunction is reported as erectile dysfunction and anorgasmia (orgasmic dysfunction). Female arousal disorder is not disclosed. The study reports that all four patients responded positively, however, the authors reserve drawing conclusions on the usefulness of sildenafil in treating antidepressant induced sexual dysfunction pending randomized placebo-controlled studies.

Thus, the limited studies of sildenafil to treat female sexual dysfunction have focused primarily on antidepressant induced sexual dysfunction (primarily indicative of orgasmic dysfunction and sexual desire dysfunction) and have lead to inconclusive results.

It has been discovered that the compounds of structural formula (I) are highly effective in treating female arousal disorders. Accordingly, the present invention provides methods of treating female arousal disorder, which comprise administering a compound of formula (I) to a patient in need thereof. Such methods are novel and unsuggested by the prior art.

SUMMARY OF THE INVENTION

The present invention provides a method of treating female arousal disorder (FAD) in a female patient, which comprises orally administering to said patient a pharmaceutically effective amount of an agent that inhibits cyclic guanosine 3'5'-monophosphate specific phosphodiesterase type 5.

The invention further provides a method of treating a female patient suffering from female arousal disorder comprising inhibiting cyclic guanosine 3'5'-monophosphate specific phosphodiesterase type 5 a sufficient amount to enhance genital and vaginal blood flow in said patient.

The invention also provides for the use of a PDE5 inhibitor to treat female arousal disorder.

DETAILED DESCRIPTION OF THE INVENTION

For the purposes of the present invention, as disclosed and claimed herein, the following terms are defined as follows:

The phrase "female arousal disorder" (FAD) as used herein refers to a condition characterized by an inability or delay in becoming aroused, or a failure to maintain an aroused state. Symptoms of the condition include a lack of genital or somatic responses such as throbbing, tingling, lubrication, and the subjective feelings of excitement and arousal. It is a subtype of female sexual dysfunction, and is largely independent of desire and orgasm. Patients likely to respond to therapy have experienced successful sexual experiences and have acquired the disorder through any number of organic factors, psychogenic factors, or other unknown reasons.

The term "$IC_{50}$" is the measure of potency of a compound to inhibit an enzyme, e.g., the PDE5 enzyme (PDE5). The $IC_{50}$ value is the concentration of a compound that results in 50% enzyme inhibition, in a single dose response experiment. Determining the $IC_{50}$ value for a compound is readily carried out by known in vitro methodology generally described in Y. Cheng et al., *Biochem Pharmacology* 22:3099–108 (1973).

The term "inhibiting" or "inhibits" refers to blocking the enzymatic activity of cyclic guanosine 3'5'-monophosphate specific phosphodiesterase type 5 to a sufficient degree to enhance genital and vaginal blood flow and produce a clinically significant response.

The phrase "orally administering" refers to the administration of a PDE5 inhibitor by any number of recognized oral dosage forms, including liquid dosage forms, tablets, capsules, gel-caps, and the like.

The term "PDE5 inhibitor" means an agent that inhibits cyclic guanosine 3'5'-monophosphate specific phosphodiesterase type 5 (PDE5) enzyme and has an $IC_{50}$ value against PDE5 of 10 nM or less.

The term "a pharmaceutically effective amount" represents an amount of a compound that is capable of inhibiting PDE5 in females and causes in clinically significant response. The clinical response includes an improvement in the condition treated or in the prevention of the condition. The particular dose of the compound administered according to this invention will, of course, be determined by the particular circumstances surrounding the case, including the compound administered, the particular condition being treated and similar considerations.

The term "agent" refers to a chemical compound suitable for pharmaceutical use.

As noted above, the present invention provides the use of a compound of formula (I) that inhibits cyclic guanosine 3'5'-monophosphate specific phosphodiesterase type 5 for treating female arousal disorder (FAD). The method comprises orally administering a pharmaceutical formulation comprising a PDE5 inhibitor to the female patient.

The compounds of structural formula (I), and their methods of manufacture, are disclosed in Daugan U.S. Pat. No. 5,859,006 and Daugan et al. U.S. Pat. No. 5,981,527, each incorporated herein by reference:

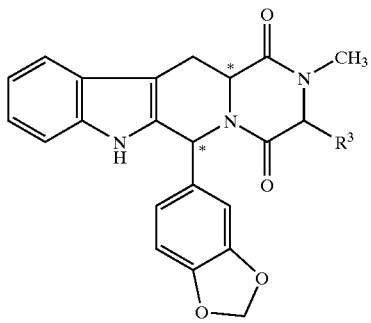

(I)

and salts and solvates (e.g., hydrates) thereof, wherein $R^3$ is hydrogen or methyl.

The compounds of structural formula (I) include:

(6R,12aR)-2,3,6,7,12,12a-hexahydro-2-methyl-6-(3,4-methylenedioxyphenyl)pyrazino[2',1':6,1]pyrido[3,4-b]indole-1,4-dione;

(3S,6R,12aR)-2,3,6,7,12,12a-hexahydro-2,3-dimethyl-6-(3,4-methylenedioxyphenyl)pyrazino[2°,1':6,1]pyrido[3,4-b]indole-1,4-dione;

physiologically acceptable solvates thereof, and mixtures thereof.

Compounds of structural formula (I), and their preparation, are disclosed in U.S. Pat. No. 5,859,006, incorporated herein by reference, and are particularly advantageous due to their selectivity for PDE5.

The methods of the present invention can be carried out by incorporating a compound of formula,(I) into a suitable formulation and administering a pharmaceutically acceptable amount of the PDE5 inhibitor to a patient in need thereof. Any pharmaceutically acceptable excipients for oral use are suitable for preparation of such formulations. Suitable pharmaceutical formulations include those described in WO 96/38131. Preferably, the formulations comprise generally recognized as safe pharmaceutical excipients such as lactose, microcrystalline cellulose, starch, calcium carbonate, magnesium stearate, stearic acid, talc, and colloidal silicon dioxide.

The formulations are prepared by standard pharmaceutical manufacturing techniques as described in *Remington's Pharmaceutical Sciences*, 18*th Ed.*, Mack Publishing Co., Easton, Pa. (1990). Such techniques include, for example, wet granulation followed by drying, milling, and compression into tablets with or without film coating; dry granulation followed by milling and compression into tablets, with or without film coating; dry blending followed by compression into tablets, with or with film coating; molded tablets; wet granulation, dried, and filled into gelatin capsules; dry blend filled into gelatin capsules; or suspension and solution filled into gelatin capsules. Generally, the solid dosage forms have identifying marks which are debossed or imprinted on the surface.

The PDE5 inhibitor is administered orally in an amount that is capable of inhibiting PDE5 in females and causing a clinically significant response. The clinical response includes an improvement in the condition treated or in the prevention of the condition. The particular dose of the compound administered according to this invention, of The extragranular croscarmellose sodium and sodium lauryl sulfate, and the Colloidal anhydrous silica were passed through a suitable sieve (e.g., 500 micron), added to the mixer and blended 5 minutes. Magnesium stearate was added and blended for 2 minutes. The blend was compressed to a target compression/weight of 250 mg using 9 mm round normal concave tooling.

The core tablets were coated with an aqueous suspension of Opadry OY-S-7322 using an Accelacota (or similar coating pan) using inlet air at 50° C. to 70° C. until the tablet weight was increased by approximately 8 mg.

| Component | Formulations (mg per tablet) | |
| --- | --- | --- |
| Agent (PDE5 inhibitor) | 1 | 5 |
| Hydroxypropyl methylcellulose phthalate | 1 | 5 |
| Microcrystalline cellulose | 221.87 | 213.87 |
| Croscarmellose sodium | 5.00 | 5.00 |
| Sodium lauryl sulfate | 2.50 | 2.50 |
| Povidone K30 | 9.38 | 9.38 |
| Purified water, USP (water for irrigation) | q.s. | q.s. |
| Croscarmellose sodium | 5.00 | 5.00 |
| Sodium lauryl sulfate | 2.50 | 2.50 |
| Colloidal anhydrous silica | 0.50 | 0.05 |
| Magnesium stearate | 1.25 | 1.25 |
| Total core subtotal (film coat opadry OY-S-7322) | 250.00 | 250.00 |

Opadry OY-S-7322 contains methylhydroxypropylcellulose Ph.Eur., titanium dioxide Ph.Eur, Triacetin course, is determined by the particular circumstances surrounding the case, including the compound administered, the severity of the condition being treated, and similar considerations. Preferably, the dose is 1 to 400 mg, and more preferably a 1 to 20 mg dose, as needed, up to the total dose for the day. Preferably, the dose administered is 5 to 20 mg/day, and most preferably a 10 mg dose is administered once per day, as needed.

The following preparations and examples are presented to further illustrate the method of the claimed invention. The scope of the present invention is not to be construed as merely consisting of the following preparation and examples.

Preparation 1

(6R,12aR)-2,3,6,7,12,12a-hexahydro-2-methyl-6-(3,4-methylenedioxyphenyl)pyrazino-[2',1':6,1]pyrido[3,4-b]indole-1,4-dione was prepared as described in U.S. Pat. No. 5,859,006, and formulated into tablets using wet granulation. Povidone was dissolved in water to make a 10% solution. The active compound, microcrystalline cellulose, croscarmellose sodium, and sodium lauryl sulfate were added to a high shear mixer, and mixed for 2 minutes. The powders were wet granulated with the povidone solution and extra water as required to complete the granulation. The resultant mixture was dried in a fluid bed drier with inlet air at 70° C.±5° C. until the loss on drying was below 2.5%. The granules were passed through a Comil with a suitable screen (or a sieve) and added to a suitable mixer. USP. Opadry increases the weight of each tablet to about 258 mg. The amount of film coat applied per tablet can be less than that stated depending on the process efficiency.

The tablets are filled into blister packs and accompanied by package insert describing the safety and efficacy of the compound.

Preparation 2

The following batch formula is used in preparing the finished dosage form.

| Ingregient | Quantity (mg) |
|---|---|
| Granulation | |
| Agent (PDE5 inhibitor) | 10.00 |
| Lactose monohydrate | 153.80 |
| Lactose monohydrate (spray Dried) | 25.00 |
| Hydroxypropylcellulose | 4.00 |
| Croscarmellose sodium | 9.00 |
| Hydroxypropylcellulose | 1.75 |
| Sodium lauryl sulfate | 0.70 |
| Outside Powders | |
| Microcrystalline cellulose | 37.50 |
| Croscarmellose sodium | 7.00 |
| Magnesium stearate | 1.25 |
| Total | 250 mg |
| Film Coat (approximately) | 11.25 mg |

Purified Water, USP is used in the manufacture of these tablets. Water is removed during processing and minimal levels remain in the finished product. Tablets are manufactured using a wet granulation process. A step-by-step description of the process follows:

The drug and excipients to be granulated are security sieved. The active agent is dry blended with lactose monohydrate (spray dried), hydroxypropyl cellulose, croscarmellose sodium, and lactose monohydrate. The resulting powder blend is granulated with an aqueous solution of hydroxypropyl cellulose and sodium lauryl sulfate using a Powerex high shear granulator. Additional water may be added to reach the desired endpoint. A mill may be used to delump the wet granulation and facilitate drying. The wet granulation is dried using either a fluid bed dryer or drying oven. Once the material is dried, it may be sized to eliminate any large agglomerates. Microcrystalline cellulose, croscarmellose sodium, and magnesium stearate are security sieved and added to the dry sized granules. These excipients and the dry granulation are mixed until uniform using a tumble bin, ribbon mixer, or other suitable mixing equipment. The mixing process may be separated into two phases; the microcrystalline cellulose, croscarmellose sodium and the dried granulation are added to the mixer and blended during the first phase, followed by the addition of the magnesium stearate to this granulation and a second mixing phase.

The mixed granulation is then compressed into tablets using a rotary compression machine. The core tablets are film coated with an aqueous suspension of the appropriate color mixture in a coating pan (e.g., Accela Cota). The coated tablets may be lightly dusted with talc to improve tablet handling characteristics.

EXAMPLE 1

FAD Clinical Studies

The use of an agent that inhibits PDE5 for the treatment of female arousal disorder is demonstrated in a clinical study assessing the physiological effect of the agent in enhancing genital blood flow in the presence of sexual stimulation and measuring clinical endpoints for assessing improvement in arousal. This study is a double-blinded placebo controlled crossover study in normal, healthy woman. Patients are administer study drug (at doses from 1 to 20 mg) or placebo. After administration, the patients are exposed to a variety of stimuli including visual, tactile, or olfactory stimuli. Endpoints assessed include altered vaginal blood flow as measured using a vaginal photoplethysmography amplitude (VPA). Subjective endpoints of genital response (throbbing, tingling, and arousal) are measured.

EXAMPLE 2

FAD Clinical Studies

The use of an agent that inhibits PDE5 for the treatment of female arousal disorder is demonstrated in a clinical study assessing the physiological effect of the agent in enhancing genital blood flow in the presence of sexual stimulation and measuring clinical endpoints for assessing improvement in arousal. The study is conducted in women suffering from mild to moderate acquired female arousal disorder. The study is a double-blinded, placebo controlled study in 200 woman. In the study, subjects receive either drug or placebo at a doses of 5 mg, 10 mg, or 20 mg (daily or on demand as needed) for up to three months. Endpoints of the study are measured using a validated questionnaire (Female Sexual Functioning Index) which assesses five domains, with one domain specifically focused on arousal. This questionnaire is given at baseline and at each monthly visit. In addition, sexual experience is evaluated using an event diary focusing on arousal and sexual satisfaction.

The present invention is based on the discovery that successful therapy is achieved through (1) proper diagnosis of patients suffering from female arousal disorder, which is a distinct subset of patients suffering from female sexual dysfunction; and (2) the use of a PDE5 inhibitor having a potency (i.e., an $IC_{50}$ versus PDE5) of 10 nM or less. Patients who suffer from female arousal disorder and respond to the methods described herein are those who have acquired an inability or delay in becoming aroused, or a failure to maintain an aroused state. Symptoms of the condition includes a lack of somatic responses such as throbbing, tingling, lubrication and the subjective feelings of excitement or arousal. Woman who suffer from female arousal disorder have experienced successful sexual experiences and have acquired the disorder through any number of organic factors, psychogenic factors or other unknown reasons. Significantly, Applicants have found that the desire is not a requisite for the treatment of arousal. Whether desire is present or not does not influence the diagnosis and treatment of female arousal disorder. However, successful treatment of FAD leads to better sexual experiences, which in turn can lead to improvement in desire and orgasm.

The principles, preferred embodiments, and modes of operation of the present invention have been described in the foregoing specification. The invention that is protected herein, however, should not be construed as limited to the particular forms disclosed, because they are to be regarded as illustrative rather than restrictive.

What is claimed is:

1. A method of treating female arousal disorder in a female patient comprising orally administering to said patient a pharmaceutically effective amount of a compound having the structural formula

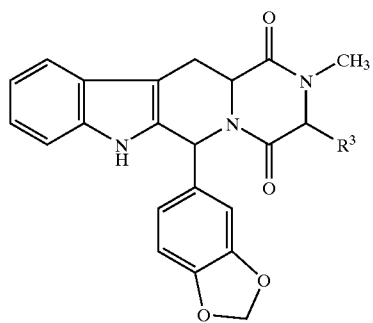

or a salt or solvate thereof, wherein R³ is hydrogen or methyl.

2. The method of claim 1 wherein the female arousal disorder is acquired female arousal disorder.

3. The method of claim 1 wherein the compound is selected from the group consisting of (6R,12aR)-2,3,6,7,12,12a-hexahydro-2-methyl-6-(3,4-methylenedioxyphenyl)pyrazino[2',1':6,1]pyrido[3,4-b]indole-1,4-dione; and (3S,6R,12aR)-2,3,6,7,12,12a-hexahydro-2,3-dimethyl-6-(3,4-methylenedioxyphenyl)pyrazino[2',1':6,1]pyrido[3,4-b]indole-1,4-dione;

a physiologically acceptable salt or solvate thereof; or a mixture thereof.

4. The method of claim 1 wherein the compound has the structure

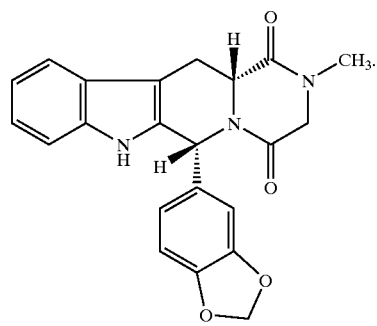

* * * * *

UNITED STATES PATENT AND TRADEMARK OFFICE
CERTIFICATE OF CORRECTION

PATENT NO. : 6,613,768 B1
DATED : September 2, 2003
INVENTOR(S) : Allemeier et al.

It is certified that error appears in the above-identified patent and that said Letters Patent is hereby corrected as shown below:

Column 3,
Line 10, "gender- (9" should be -- gender (9 --
Line 37, "did-not" should be -- did not --

Column 5,
Line 30, "[2°, 1' : 6, 1]" should be [2', 1': 6, 1] --
Line 41, "formula, (I)" should be -- formula (I) --

Column 6,
Lines 4-36, text beginning with "The" and continuing through line 36 ending with "Triacetin." should be moved to line 64, after "a suitable mixer."

Column 8,
Line 3, "woman" should be -- women --
Line 4, "Patients are administer" should be -- Patients are administered --

Signed and Sealed this

Eleventh Day of May, 2004

JON W. DUDAS
*Acting Director of the United States Patent and Trademark Office*